US012788612B2

(12) United States Patent
Hansen et al.

(10) Patent No.: US 12,788,612 B2
(45) Date of Patent: Nov. 10, 2026

(54) OSTOMY APPLIANCE WITH ELECTRODE MULTIPLEXING AND RELATED METHODS

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK); Finn Speiermann, Virum (DK); Klaus Thoegersen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 400 days.

(21) Appl. No.: 18/527,412

(22) Filed: Dec. 4, 2023

(65) Prior Publication Data

US 2024/0115411 A1 Apr. 11, 2024
US 2026/0007538 A9 Jan. 8, 2026

Related U.S. Application Data

(63) Continuation of application No. 16/955,790, filed as application No. PCT/DK2018/050384 on Dec. 20, 2018, now Pat. No. 11,872,108.

(30) Foreign Application Priority Data

Dec. 22, 2017 (DK) .......................... PA 2017 70983

(51) Int. Cl.
*A61F 5/44* (2006.01)
*A61B 5/00* (2006.01)
(Continued)

(52) U.S. Cl.
CPC .......... *A61F 5/4404* (2013.01); *A61B 5/4851* (2013.01); *A61F 5/443* (2013.01); *H04M 3/244* (2013.01); *H04Q 11/00* (2013.01)

(58) Field of Classification Search
CPC ...... A61F 5/4404; A61F 5/443; H04M 3/244; H04Q 11/00; A61B 5/4851
See application file for complete search history.

(56) References Cited

U.S. PATENT DOCUMENTS 2,054,535 A 9/1936 Diack
2,327,514 A 8/1943 Fenwick
(Continued)

FOREIGN PATENT DOCUMENTS

CA 2540756 C 1/2008
CA 3009449 C 9/2019
(Continued)

*Primary Examiner* — Brenda H Pham
(74) *Attorney, Agent, or Firm* — Coloplast Corp., Coloplast A/S; Nick Baumann

(57) ABSTRACT

A base plate for an ostomy appliance and related methods are disclosed, the base plate comprising a first adhesive layer with a proximal side configured for attachment of the base plate to the skin surface of a user a plurality of electrodes including a first electrode and a second electrode, the first electrode comprising a first connection part and the second electrode comprising a second connection part; a monitor interface for forming mechanical and electrical connection with a monitor device, the monitor interface comprising a coupling part and a plurality of terminals including a first terminal; and a multiplexer with a number of N input pins and a number of M output pins; wherein the N input pins includes a first input pin and a second input pin, and the M output pins include a first output pin, wherein the first input pin is connected to the first connection part and the second input pin is connected to the second connection part, and the first output pin is connected to the first terminal of the monitor interface, and wherein the multiplexer is configured to connect the first input pin to the first output pin in a first
(Continued)

multiplexer configuration and to connect the second input pin to the first output pin in a second multiplexer configuration.

20 Claims, 12 Drawing Sheets

(51) Int. Cl.
*A61F 5/443* (2006.01)
*H04M 3/24* (2006.01)
*H04Q 11/00* (2006.01)

(56) References Cited

U.S. PATENT DOCUMENTS 2,542,233 A 2/1951 Carroll
2,544,579 A 3/1951 Ardner
3,214,502 A 10/1965 Schaar
3,808,354 A 4/1974 Feezor et al.
3,832,510 A 8/1974 Pfau et al.
3,915,171 A 10/1975 Shermeta
3,941,133 A 3/1976 Chen
4,231,369 A 11/1980 Sorensen et al.
4,372,308 A 2/1983 Steer et al.
4,449,970 A 5/1984 Bevan et al.
4,668,227 A 5/1987 Kay
4,754,264 A 6/1988 Okada et al.
4,775,374 A 10/1988 Cilento et al.
4,834,731 A 5/1989 Nowak et al.
4,973,323 A 11/1990 Kaczmarek et al.
4,982,742 A 1/1991 Claude
5,013,307 A 5/1991 Broida
5,016,645 A 5/1991 Williams et al.
5,051,259 A 9/1991 Olsen et al.
5,074,851 A 12/1991 Plass et al.
5,111,812 A 5/1992 Swanson et al.
5,167,650 A 12/1992 Johnsen et al.
5,197,895 A 3/1993 Stupecky
5,237,995 A 8/1993 Cano
5,318,543 A 6/1994 Ross et al.
5,358,488 A 10/1994 Suriyapa
5,486,158 A 1/1996 Samuelsen
5,519,644 A 5/1996 Benton
5,570,082 A 10/1996 Mahgerefteh et al.
5,593,397 A 1/1997 La Gro
5,672,163 A 9/1997 Ferreira et al.
5,677,221 A 10/1997 Tseng
5,704,905 A 1/1998 Jensen et al.
5,790,036 A 8/1998 Fisher et al.
5,800,415 A 9/1998 Olsen
5,816,252 A 10/1998 Faries, Jr. et al.
5,834,009 A 11/1998 Sawers et al.
5,846,558 A 12/1998 Nielsen et al.
5,876,855 A 3/1999 Wong et al.
5,879,292 A 3/1999 Sternberg et al.
5,942,186 A 8/1999 Sanada et al.
6,015,399 A 1/2000 Mracna et al.
6,025,725 A 2/2000 Gershenfeld et al.
6,057,689 A 5/2000 Saadat
6,078,261 A 6/2000 Davsko
6,103,033 A 8/2000 Say et al.
6,135,986 A 10/2000 Leisner et al.
6,165,005 A 12/2000 Mills et al.
6,171,289 B1 1/2001 Millot et al.
6,206,864 B1 3/2001 Kavanagh et al.
6,241,704 B1 6/2001 Peterson et al.
6,246,330 B1 6/2001 Nielsen
6,270,445 B1 8/2001 Dean, Jr. et al.
6,297,422 B1 10/2001 Hansen et al.
6,407,308 B1 6/2002 Roe et al.
6,433,244 B1 8/2002 Roe et al.
6,482,491 B1 11/2002 Samuelsen et al.
6,485,476 B1 11/2002 von Dyck et al.
6,520,943 B1 2/2003 Wagner
6,659,989 B1 12/2003 Otto
6,764,474 B2 7/2004 Nielsen et al.
7,049,478 B1 5/2006 Smith
7,066,919 B1 6/2006 Sauerland et al.
7,150,728 B2 12/2006 Hansen et al.
7,166,091 B1 1/2007 Zeltner
7,199,501 B2 4/2007 Pei et al.
7,214,217 B2 5/2007 Pedersen et al.
7,221,279 B2 5/2007 Nielsen
7,326,190 B2 2/2008 Botten
7,341,578 B2 3/2008 Bulow et al.
7,347,844 B2 3/2008 Cline et al.
7,367,965 B2 5/2008 Poulsen et al.
7,422,578 B2 9/2008 Shan et al.
7,559,922 B2 7/2009 Botten
7,625,362 B2 12/2009 Boehringer et al.
7,641,612 B1 1/2010 McCall
7,670,289 B1 3/2010 McCall
7,943,812 B2 5/2011 Stroebeck et al.
7,981,098 B2 7/2011 Boehringer et al.
8,061,360 B2 11/2011 Locke et al.
8,277,427 B2 10/2012 Edvardsen et al.
8,319,003 B2 11/2012 Olsen et al.
8,326,051 B1 12/2012 Hobbs
8,398,575 B1 3/2013 McCall
8,398,603 B2 3/2013 Thirstrup et al.
8,399,732 B2 3/2013 Oelund et al.
8,409,158 B2 4/2013 Edvardsen et al.
8,449,471 B2 5/2013 Tran
8,474,338 B2 7/2013 Gelman et al.
8,500,718 B2 8/2013 Locke et al.
8,632,492 B2 1/2014 DeLegge
8,680,991 B2 3/2014 Tran
8,684,982 B2 4/2014 Nguyen-DeMary et al.
8,740,865 B2 6/2014 Krystek et al.
8,795,257 B2 8/2014 Coulthard et al.
D712,545 S 9/2014 Igwebuike et al.
8,821,464 B2 9/2014 Hanuka et al.
8,975,465 B2 3/2015 Hong et al.
8,979,813 B2 3/2015 Uveborn
9,046,085 B2 6/2015 Schoess et al.
9,066,812 B2 6/2015 Edvardsen et al.
9,216,104 B2 12/2015 Thirstrup et al.
9,308,332 B2 4/2016 Heppe
9,322,797 B1 4/2016 Lastinger et al.
9,566,383 B2 2/2017 Yodfat et al.
9,629,779 B2 4/2017 Grum-Schwensen et al.
9,629,964 B2 4/2017 Wuepper
9,675,267 B2 6/2017 Laakkonen et al.
9,693,908 B2 7/2017 Eriksson et al.
9,770,359 B2 9/2017 Edvardsen et al.
9,788,991 B2 10/2017 Bird
9,867,934 B2 1/2018 Heppe
9,928,341 B2 3/2018 Angelides
10,016,298 B2 7/2018 Thirstrup et al.
D826,740 S 8/2018 Stevens et al.
10,426,342 B2 10/2019 Hresko et al.
10,500,084 B2 12/2019 Hansen et al.
10,531,977 B2 1/2020 Schoess et al.
10,646,370 B2 5/2020 Keleny et al.
10,792,184 B2 10/2020 Hvid et al.
10,799,385 B2 10/2020 Hansen et al.
10,849,781 B2 12/2020 Hansen et al.
10,874,541 B2 12/2020 Seres et al.
10,987,243 B2 4/2021 Thirstrup et al.
11,096,818 B2 8/2021 Thirstrup et al.
11,135,084 B2 10/2021 Seres et al.
11,238,133 B1 2/2022 Brewer et al.
11,306,224 B2 4/2022 Chatterjee et al.
11,406,525 B2 8/2022 Seres et al.
11,471,318 B2 10/2022 Hansen et al.
11,491,042 B2 11/2022 Seres et al.
11,534,323 B2 12/2022 Hansen et al.
11,540,937 B2 1/2023 Hansen et al.
11,547,595 B2 1/2023 Hansen et al.
11,547,596 B2 1/2023 Hansen et al.
11,559,423 B2 1/2023 Speiermann et al.
11,559,426 B2 1/2023 Sletten et al.
2001/0041920 A1 11/2001 Starkweather et al.
2001/0051787 A1 12/2001 Haller et al.

(56) References Cited

U.S. PATENT DOCUMENTS

2002/0013613 A1 1/2002 Haller et al.
2002/0019615 A1 2/2002 Roe et al.
2002/0109621 A1 8/2002 Khair et al.
2003/0132763 A1 7/2003 Ellenz
2003/0169032 A1 9/2003 Minchole et al.
2004/0006320 A1 1/2004 Buglino et al.
2004/0030305 A1 2/2004 Sakamoto
2004/0036484 A1 2/2004 Tamai
2004/0049145 A1 3/2004 Flick
2004/0068244 A1 4/2004 Salone et al.
2004/0078219 A1 4/2004 Kaylor et al.
2004/0100376 A1 5/2004 Lye et al.
2004/0106908 A1 6/2004 Leise, Jr. et al.
2004/0111072 A1 6/2004 McKissick
2004/0133175 A1 7/2004 Hagedorn-Olsen
2004/0171999 A1 9/2004 Andersen et al.
2004/0193122 A1 9/2004 Cline et al.
2004/0193123 A1 9/2004 Fenton
2004/0216833 A1 11/2004 Fleming et al.
2005/0054997 A1 3/2005 Buglino et al.
2005/0065488 A1 3/2005 Elliott
2005/0070863 A1 3/2005 Bulow et al.
2005/0085779 A1 4/2005 Poulsen et al.
2005/0101841 A9 5/2005 Kaylor et al.
2005/0240163 A1 10/2005 Andersen
2005/0256545 A1 11/2005 Koh et al.
2005/0261645 A1 11/2005 Conrad et al.
2006/0015081 A1 1/2006 Suzuki et al.
2006/0025727 A1 2/2006 Boehringer et al.
2006/0052752 A1 3/2006 McMichael
2006/0194324 A1 8/2006 Faries, Jr. et al.
2006/0271002 A1 11/2006 Botten
2007/0010256 A1 1/2007 Klabunde et al.
2007/0035405 A1 2/2007 Wada et al.
2007/0135782 A1 6/2007 Bager et al.
2007/0185464 A1 8/2007 Fattman et al.
2007/0204691 A1 9/2007 Bogner et al.
2008/0038536 A1 2/2008 Strobech et al.
2008/0041792 A1 2/2008 Crnkovich et al.
2008/0071214 A1 3/2008 Locke et al.
2008/0075934 A1 3/2008 Barlow, Jr. et al.
2008/0091154 A1 4/2008 Botten
2008/0096726 A1 4/2008 Riley et al.
2008/0097360 A1 4/2008 Andersen et al.
2008/0140057 A1 6/2008 Wood et al.
2008/0234641 A1 9/2008 Locke et al.
2008/0275327 A1 11/2008 Faarbaek et al.
2008/0278337 A1 11/2008 Huang et al.
2008/0300559 A1 12/2008 Gustafson et al.
2008/0300578 A1 12/2008 Freedman
2008/0306459 A1 12/2008 Albrectsen
2009/0012501 A1 1/2009 Boehringer et al.
2009/0118600 A1 5/2009 Ortiz et al.
2009/0118687 A1 5/2009 Kristensen et al.
2009/0167286 A1 7/2009 Naylor et al.
2009/0173935 A1 7/2009 Cho et al.
2009/0216169 A1 8/2009 Hansen et al.
2009/0227969 A1 9/2009 Jaeb et al.
2009/0234916 A1 9/2009 Cosentino et al.
2009/0247970 A1 10/2009 Keleny et al.
2009/0264957 A1 10/2009 Giftakis et al.
2010/0010460 A1 1/2010 Butler
2010/0030167 A1 2/2010 Thirstrup et al.
2010/0036206 A1 2/2010 Lorio
2010/0072271 A1 3/2010 Thorstensson
2010/0076275 A1 3/2010 Chu et al.
2010/0106220 A1 4/2010 Ecker et al.
2010/0114047 A1 5/2010 Song et al.
2010/0271212 A1 10/2010 Page
2010/0311167 A1 12/2010 Wood et al.
2011/0034890 A1 2/2011 Stroebech et al.
2011/0077497 A1 3/2011 Oster et al.
2011/0130642 A1 6/2011 Jaeb et al.
2011/0245682 A1 10/2011 Robinson et al.
2011/0246983 A1 10/2011 Brunet et al.
2011/0257496 A1 10/2011 Terashima et al.
2012/0013130 A1 1/2012 Jung
2012/0143154 A1 6/2012 Edvardsen et al.
2012/0143155 A1 6/2012 Edvardsen et al.
2012/0253224 A1 10/2012 Mir et al.
2012/0258302 A1 10/2012 Hunt et al.
2012/0259230 A1 10/2012 Riley
2012/0283678 A1 11/2012 Nguyen-DeMary et al.
2012/0304767 A1 12/2012 Howard et al.
2013/0018231 A1 1/2013 Hong et al.
2013/0030167 A1 1/2013 Wang et al.
2013/0030397 A1 1/2013 Sabeti
2013/0060213 A1 3/2013 Hanuka et al.
2013/0066285 A1 3/2013 Locke et al.
2013/0072886 A1 3/2013 Schertiger et al.
2013/0078912 A1 3/2013 San Vicente et al.
2013/0086217 A1 4/2013 Price et al.
2013/0102979 A1 4/2013 Coulthard et al.
2013/0138065 A1 5/2013 Buus
2013/0150769 A1 6/2013 Heppe
2013/0165862 A1 6/2013 Griffith et al.
2013/0192604 A1 8/2013 Persson et al.
2013/0226116 A1 8/2013 Edvardsen et al.
2013/0231620 A1 9/2013 Thirstrup et al.
2013/0261575 A1 10/2013 Kiyoshi
2013/0267790 A1 10/2013 Pfuetzner et al.
2013/0303867 A1 11/2013 Elfstrom et al.
2013/0324952 A1 12/2013 Krystek et al.
2013/0324955 A1 12/2013 Wong et al.
2014/0051946 A1 2/2014 Arne et al.
2014/0128815 A1 5/2014 Cabiri et al.
2014/0200426 A1 7/2014 Taub et al.
2014/0200538 A1 7/2014 Euliano et al.
2014/0236111 A1 8/2014 Casado et al.
2014/0236335 A1 8/2014 Lewis et al.
2014/0275854 A1 9/2014 Venkatraman et al.
2014/0276501 A1 9/2014 Cisko
2014/0288381 A1 9/2014 Faarbaek et al.
2014/0303574 A1 10/2014 Knutson
2014/0309600 A1 10/2014 Aceto et al.
2014/0323909 A1 10/2014 Kim
2014/0327433 A1 11/2014 Anway et al.
2014/0336493 A1 11/2014 Kulach et al.
2015/0057634 A1 2/2015 Mastrototaro et al.
2015/0150457 A1 6/2015 Wu et al.
2015/0151051 A1 6/2015 Tsoukalis
2015/0230706 A1 8/2015 Nakagawa et al.
2015/0231802 A1 8/2015 Quan et al.
2015/0250639 A1 9/2015 Thirstrup et al.
2015/0257923 A1 9/2015 Thirstrup et al.
2015/0328389 A1 11/2015 Heppe
2015/0342777 A1 12/2015 Seres et al.
2015/0351690 A1 12/2015 Toth et al.
2015/0374896 A1 12/2015 Du et al.
2016/0008182 A1 1/2016 Prokopuk et al.
2016/0015570 A1 1/2016 Heinecke et al.
2016/0058604 A1 3/2016 Wiltshire et al.
2016/0084869 A1 3/2016 Yuen et al.
2016/0103966 A1 4/2016 Mirza
2016/0117062 A1 4/2016 Hussam et al.
2016/0158056 A1 6/2016 Davis et al.
2016/0158517 A1 6/2016 Nebbia
2016/0158969 A1 6/2016 McLane et al.
2016/0166438 A1 6/2016 Rovaniemi
2016/0178387 A1 6/2016 Yamasaki et al.
2016/0218555 A1 7/2016 Slaby et al.
2016/0235581 A1 8/2016 Keleny et al.
2016/0242654 A1 8/2016 Quinlan et al.
2016/0278990 A1 9/2016 Chen
2016/0284084 A1 9/2016 Gurcan et al.
2016/0305776 A1 10/2016 Mårtensson et al.
2016/0310077 A1 10/2016 Hunter et al.
2016/0310140 A1 10/2016 Belson et al.
2016/0310329 A1 10/2016 Patel et al.
2016/0317728 A1 11/2016 Lewis et al.
2016/0324442 A1* 11/2016 Zdeblick ................ A61B 5/073
2016/0331232 A1 11/2016 Love et al.
2016/0361015 A1 12/2016 Wang et al.
2017/0042614 A1 2/2017 Salahieh et al.

(56) References Cited

U.S. PATENT DOCUMENTS

2017/0050004 A1 2/2017 Tilson et al.
2017/0055896 A1 3/2017 Al-Ali et al.
2017/0079530 A1 3/2017 DiMaio et al.
2017/0079576 A1 3/2017 Stroebech et al.
2017/0098044 A1 4/2017 Lai et al.
2017/0112658 A1 4/2017 Hosono
2017/0113001 A1 4/2017 Trock
2017/0140103 A1 5/2017 Angelides
2017/0156920 A1 6/2017 Hunt et al.
2017/0181628 A1 6/2017 Burnette et al.
2017/0262986 A1 9/2017 Xiong et al.
2017/0319073 A1 11/2017 DiMaio et al.
2017/0340474 A1 11/2017 Thirstrup et al.
2017/0340498 A1 11/2017 Tessmer et al.
2017/0348137 A1 12/2017 Hvid et al.
2017/0360592 A1 12/2017 Carrubba
2017/0360593 A1 12/2017 Cox
2018/0021164 A1 1/2018 Fenton
2018/0021165 A1 1/2018 Fenton
2018/0049667 A1 2/2018 Heppe
2018/0055359 A1 3/2018 Shamim et al.
2018/0078163 A1 3/2018 Welch
2018/0109852 A1 4/2018 Mandapaka et al.
2018/0110078 A1 4/2018 Mandapaka et al.
2018/0136712 A1 5/2018 Niikura et al.
2018/0171183 A1 6/2018 Sakurai et al.
2018/0177626 A1 6/2018 Israelson
2018/0250156 A1 9/2018 Lam
2018/0298240 A1 10/2018 Chatterjee et al.
2018/0318475 A1 11/2018 Thomson et al.
2018/0344533 A1 12/2018 Rovaniemi
2019/0008439 A1 1/2019 Sageder et al.
2019/0099552 A1 4/2019 Zhang et al.
2019/0133810 A1 5/2019 Seres et al.
2019/0133811 A1 5/2019 Seres et al.
2019/0133812 A1 5/2019 Seres et al.
2019/0142623 A1 5/2019 Schoess et al.
2019/0175386 A1 6/2019 Monty
2019/0184093 A1 6/2019 Sjolund et al.
2019/0192066 A1 6/2019 Schoess et al.
2019/0192332 A1 6/2019 Hansen et al.
2019/0192333 A1 6/2019 Hansen et al.
2019/0192334 A1 6/2019 Hansen et al.
2019/0240059 A1 8/2019 Seres et al.
2019/0247050 A1 8/2019 Goldsmith
2019/0374163 A1 12/2019 Faarbaek et al.
2019/0374372 A1 12/2019 Seres et al.
2020/0100931 A1 4/2020 Schoess et al.
2020/0188161 A1 6/2020 Seres et al.
2020/0246174 A1 8/2020 Hansen et al.
2020/0246175 A1 8/2020 Hansen et al.
2020/0246176 A1 8/2020 Hansen et al.
2020/0246177 A1 8/2020 Hansen et al.
2020/0276063 A1 9/2020 Muñoz Herencia
2020/0279368 A1 9/2020 Tada et al.
2020/0297244 A1 9/2020 Brownhill et al.
2020/0306074 A1 10/2020 Speiermann et al.
2020/0322793 A1 10/2020 Yang
2020/0330258 A1 10/2020 Hansen et al.
2020/0330260 A1 10/2020 Hansen et al.
2020/0337880 A1 10/2020 Hansen et al.
2020/0337881 A1 10/2020 Hansen et al.
2020/0337882 A1 10/2020 Hansen et al.
2020/0337883 A1 10/2020 Hansen et al.
2020/0375499 A1 12/2020 Hansen et al.
2020/0375782 A1 12/2020 Hansen et al.
2020/0375783 A1 12/2020 Hansen et al.
2020/0375784 A1 12/2020 Hansen et al.
2020/0375785 A1 12/2020 Hansen et al.
2020/0375786 A1 12/2020 Hansen et al.
2020/0375809 A1 12/2020 Sullivan et al.
2020/0383637 A1 12/2020 Hansen et al.
2020/0383818 A1 12/2020 Hansen et al.
2020/0383819 A1 12/2020 Sletten et al.
2020/0383820 A1 12/2020 Hansen et al.
2020/0383821 A1 12/2020 Hansen et al.
2020/0390587 A1 12/2020 Svanegaard et al.
2020/0390588 A1 12/2020 Hansen et al.
2020/0390589 A1 12/2020 Hansen et al.
2020/0395120 A1 12/2020 Svanegaard et al.
2020/0395610 A1 12/2020 Ono et al.
2020/0405228 A1 12/2020 Svanegaard et al.
2020/0405229 A1 12/2020 Svanegaard et al.
2020/0405230 A1 12/2020 Svanegaard et al.
2021/0000414 A1 1/2021 Svanegaard et al.
2021/0000633 A1 1/2021 Hansen et al.
2021/0000634 A1 1/2021 Svanegaard et al.
2021/0000635 A1 1/2021 Hansen et al.
2021/0000636 A1 1/2021 Hansen et al.
2021/0007663 A1 1/2021 Svanegaard et al.
2021/0007881 A1 1/2021 Svanegaard et al.
2021/0015653 A1 1/2021 Hansen et al.
2021/0015654 A1 1/2021 Hansen et al.
2021/0022683 A1 1/2021 Faarbaek et al.
2021/0038424 A1 2/2021 Svanegaard et al.
2021/0059603 A1 3/2021 Svanegaard et al.
2021/0085511 A1 3/2021 Hansen et al.
2021/0085512 A1 3/2021 Hansen et al.
2021/0100533 A1 4/2021 Seres et al.
2021/0128364 A1 5/2021 Cole et al.
2021/0177642 A1 6/2021 Andersen et al.
2021/0212855 A1 7/2021 Hansen et al.
2021/0228194 A1 7/2021 Mayberg
2021/0338471 A1 11/2021 Nolan et al.
2021/0361464 A1 11/2021 Larsen et al.
2021/0361465 A1 11/2021 Hansen et al.
2021/0361466 A1 11/2021 Hansen et al.
2021/0361467 A1 11/2021 Hansen et al.
2021/0369197 A1 12/2021 Hansen et al.
2021/0369488 A1 12/2021 Hansen et al.
2021/0369489 A1 12/2021 Hansen et al.
2021/0369490 A1 12/2021 Hansen et al.
2021/0370217 A1 12/2021 Kirschman
2021/0386368 A1 12/2021 Carlsson et al.
2022/0000652 A1 1/2022 Thirstrup et al.
2022/0031227 A1 2/2022 Cho et al.
2022/0031495 A1 2/2022 Seres et al.
2022/0079802 A1 3/2022 Hansen
2022/0079803 A1 3/2022 Windeballe et al.
2022/0087851 A1 3/2022 Stroebech
2022/0110585 A1 4/2022 Andersen
2022/0117771 A1 4/2022 Fearn et al.
2022/0142807 A1 5/2022 Tofte
2022/0192860 A1 6/2022 Hansen et al.
2022/0241104 A1 8/2022 Knoedler
2022/0241105 A1 8/2022 Hansen et al.
2022/0265458 A1 8/2022 Carlsson et al.
2022/0378602 A1 12/2022 Hansen et al.
2023/0059470 A1 2/2023 Hansen et al.
2023/0064734 A1 3/2023 Hansen et al.
2023/0105402 A1 4/2023 Hansen et al.
2023/0117727 A1 4/2023 Hansen et al.
2023/0118594 A1 4/2023 Speiermann et al.
2023/0145670 A1 5/2023 Seres et al.
2023/0190509 A1 6/2023 Hansen et al.
2023/0210682 A1 7/2023 Hansen et al.
2023/0233147 A1 7/2023 Hansen et al.
2023/0329893 A1 10/2023 Olsen et al.
2023/0338005 A1 10/2023 Barthe et al.

FOREIGN PATENT DOCUMENTS

CA 3002372 C 3/2021
CA 2947016 C 2/2023
CN 203786580 U 8/2014
CN 104902399 A 9/2015
CN 104980878 A 10/2015
CN 105588856 A 5/2016
CN 206271160 U 6/2017
CN 206450708 U 8/2017
CN 107661167 A 2/2018
CN 105615896 B 5/2019
CN 105359167 B 6/2019
DE 3437950 A1 4/1985

(56) References Cited

FOREIGN PATENT DOCUMENTS

| | | | |
|---|---|---|---|
| DE | 3836590 | A1 | 5/1990 |
| DE | 19900611 | C1 | 7/2000 |
| DE | 69722993 | | 7/2003 |
| DE | 102011014321 | A1 | 9/2012 |
| DE | 102011076219 | A1 | 11/2012 |
| EP | 0168967 | A1 | 1/1986 |
| EP | 0373782 | B1 | 10/1994 |
| EP | 0416397 | B1 | 5/1995 |
| EP | 0800804 | B1 | 6/2003 |
| EP | 1188157 | B1 | 12/2005 |
| EP | 2108345 | A1 | 10/2009 |
| EP | 1275357 | B1 | 3/2011 |
| EP | 2000083 | B1 | 8/2012 |
| EP | 2601915 | A1 | 6/2013 |
| EP | 2738960 | A1 | 6/2014 |
| EP | 2489561 | B1 | 8/2014 |
| EP | 2453851 | B1 | 10/2014 |
| EP | 2654646 | B1 | 7/2016 |
| EP | 3213727 | B1 | 12/2019 |
| EP | 3064179 | B1 | 9/2021 |
| EP | 3226946 | B1 | 8/2023 |
| GB | 2219679 | A | 12/1989 |
| GB | 2308306 | B | 9/1999 |
| GB | 2343628 | B | 10/2000 |
| GB | 2465742 | B | 7/2012 |
| GB | 2486968 | B | 2/2015 |
| GB | 2542093 | A | 3/2017 |
| GB | 2561193 | B | 9/2020 |
| JP | H0474882 | A | 3/1992 |
| JP | H06152077 | A | 5/1994 |
| JP | H0910184 | A | 1/1997 |
| JP | 2000093448 | A | 4/2000 |
| JP | 2001087299 | A | 4/2001 |
| JP | 2002055074 | A | 2/2002 |
| JP | 2002224093 | A | 8/2002 |
| JP | 2005323981 | A | 11/2005 |
| JP | 2007319561 | A | 12/2007 |
| JP | 2009519751 | A | 5/2009 |
| JP | 2014033745 | A | 2/2014 |
| JP | 2014054368 | A | 3/2014 |
| KR | 101056989 | B1 | 8/2011 |
| KR | 20120003987 | A | 1/2012 |
| KR | 200485138 | Y1 | 12/2017 |
| NL | 1001019 | C2 | 2/1997 |
| NL | 1003904 | C2 | 3/1998 |
| RU | 2527155 | C2 | 8/2014 |
| TW | 201201783 | A | 1/2012 |
| WO | 1994015562 | A1 | 7/1994 |
| WO | 1997010012 | A1 | 3/1997 |
| WO | 1999033037 | A1 | 7/1999 |
| WO | 1999036017 | A1 | 7/1999 |
| WO | 2000079497 | A1 | 12/2000 |
| WO | 2001013830 | A1 | 3/2001 |
| WO | 2001050996 | A1 | 7/2001 |
| WO | 2002052302 | A2 | 7/2002 |
| WO | 2002099765 | A1 | 12/2002 |
| WO | 2005038693 | A1 | 4/2005 |
| WO | 2005082271 | A2 | 9/2005 |
| WO | 2006008866 | A1 | 1/2006 |
| WO | 2006094513 | A2 | 9/2006 |
| WO | 2007000168 | A1 | 1/2007 |
| WO | 2007059774 | A2 | 5/2007 |
| WO | 2007070266 | A1 | 6/2007 |
| WO | 2007098762 | A1 | 9/2007 |
| WO | 2007128038 | A1 | 11/2007 |
| WO | 2007133555 | A2 | 11/2007 |
| WO | 2008057884 | A2 | 5/2008 |
| WO | 2009006900 | A1 | 1/2009 |
| WO | 2009052496 | A1 | 4/2009 |
| WO | 2009107011 | A1 | 9/2009 |
| WO | 2009112912 | A2 | 9/2009 |
| WO | 2011003421 | A1 | 1/2011 |
| WO | 2011004165 | A1 | 1/2011 |
| WO | 2011061540 | A1 | 5/2011 |
| WO | 2011105701 | A2 | 9/2011 |
| WO | 2011123018 | A1 | 10/2011 |
| WO | 2011139499 | A1 | 11/2011 |
| WO | 2011161254 | A2 | 12/2011 |
| WO | 2012068386 | A1 | 5/2012 |
| WO | 2012076022 | A2 | 6/2012 |
| WO | 2012084987 | A2 | 6/2012 |
| WO | 2013013197 | A1 | 1/2013 |
| WO | 2013095231 | A1 | 6/2013 |
| WO | 2014004207 | A1 | 1/2014 |
| WO | 2014086369 | A1 | 6/2014 |
| WO | 2015007284 | A1 | 1/2015 |
| WO | 2015014774 | A1 | 2/2015 |
| WO | 2015084462 | A1 | 6/2015 |
| WO | 2015094064 | A1 | 6/2015 |
| WO | 2015187366 | A1 | 12/2015 |
| WO | 2016132738 | A1 | 8/2016 |
| WO | 2016162038 | A1 | 10/2016 |
| WO | 2016166731 | A1 | 10/2016 |
| WO | 2016192738 | A1 | 12/2016 |
| WO | 2017023794 | A1 | 2/2017 |
| WO | 2017062042 | A1 | 4/2017 |
| WO | 2017067558 | A1 | 4/2017 |
| WO | 2017067560 | A1 | 4/2017 |
| WO | 2017074505 | A1 | 5/2017 |
| WO | 2017088153 | A1 | 6/2017 |
| WO | 2017108109 | A1 | 6/2017 |
| WO | 2017136696 | A1 | 8/2017 |
| WO | 2017190752 | A1 | 11/2017 |
| WO | 2018028756 | A1 | 2/2018 |
| WO | 2019094635 | A1 | 5/2019 |
| WO | 2019120432 | A1 | 6/2019 |
| WO | 2019161859 | A1 | 8/2019 |
| WO | 2019161860 | A1 | 8/2019 |
| WO | 2019161863 | A1 | 8/2019 |
| WO | 2019174693 | A1 | 9/2019 |
| WO | 2019174695 | A1 | 9/2019 |
| WO | 2019213623 | A1 | 11/2019 |
| WO | 2020035121 | A1 | 2/2020 |

* cited by examiner

OSTOMY APPLIANCE WITH ELECTRODE MULTIPLEXING AND RELATED METHODS

The present disclosure relates to an ostomy system, devices thereof and methods related thereto, e.g. method of monitoring an ostomy appliance and/or method of manufacturing a base plate of an ostomy appliance. The ostomy appliance system comprises an ostomy appliance and an ostomy monitor device. In particular, the present disclosure relates to a base plate for an ostomy appliance for monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
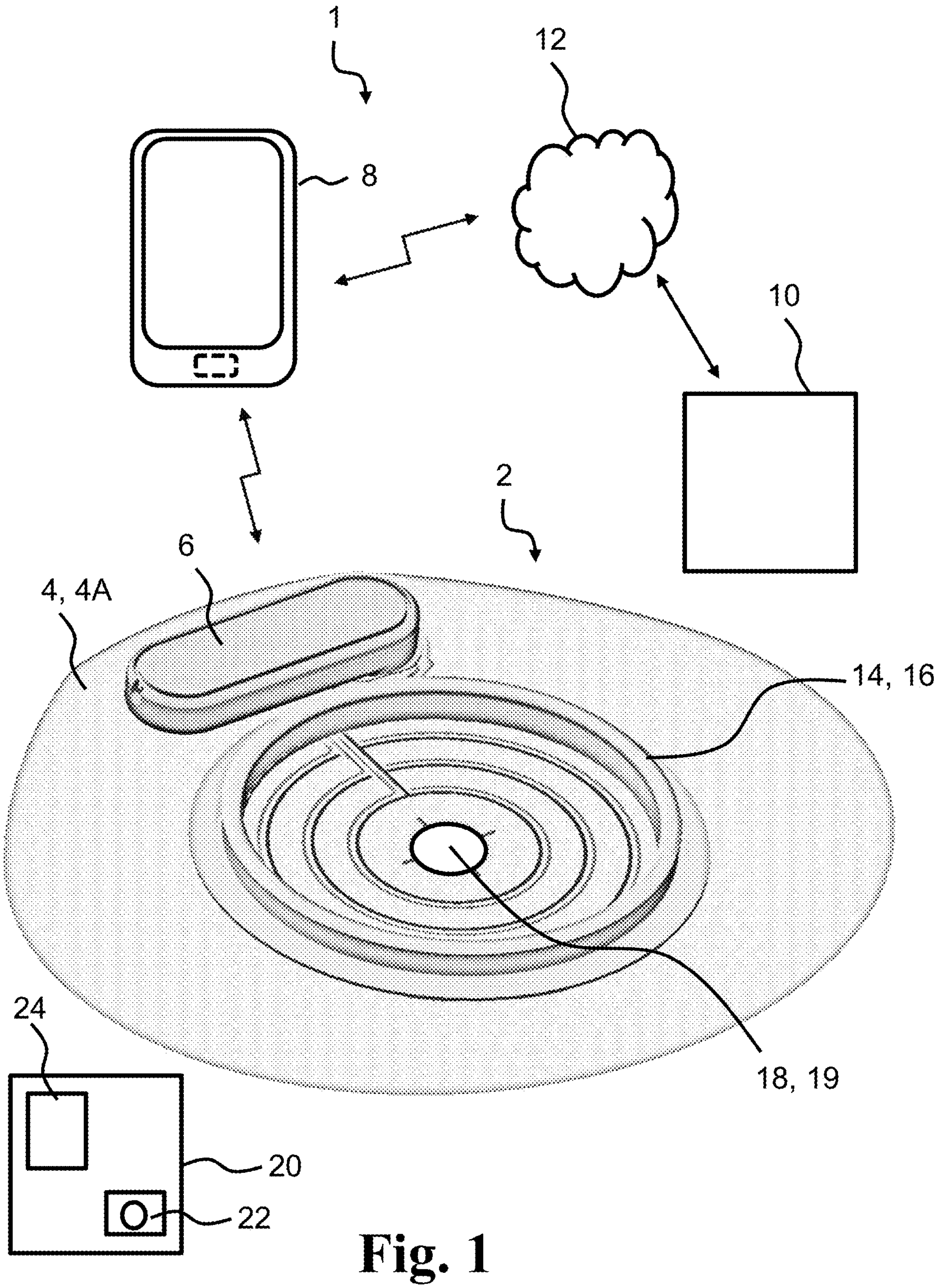
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity, and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

A base plate for an ostomy appliance is disclosed, the base plate comprising a first adhesive layer with a proximal side configured for attachment of the base plate to the skin surface of a user; a plurality of electrodes including a first electrode and a second electrode, the first electrode comprising a first connection part and the second electrode comprising a second connection part; and a monitor interface for forming mechanical and electrical connection with a monitor device, the monitor interface comprising a coupling part and a plurality of terminals including a first terminal. The base plate comprises a multiplexer with a number of N input pins and a number of M output pins; wherein the N input pins includes a first input pin and a second input pin, and the M output pins include a first output pin. The first input pin is connected to the first connection part, the second input pin is connected to the second connection part, and the first output pin is connected to the first terminal of the monitor interface. The multiplexer is configured to connect the first input pin to the first output pin in a first multiplexer configuration and to connect the second input pin to the first output pin in a second multiplexer configuration.

In one or more exemplary base plates, the number N of input pins of the multiplexer is larger than the number M of output pins of the multiplexer, i.e. N>M. In one or more exemplary base plates, the multiplexer comprises at least eight input pins and one or two output pins. In one or more exemplary base plates, the multiplexer comprises at least sixteen input pins and one or two output pins.

The monitor interface may comprise a second terminal, and the M output pins may include a second output pin connected to the second terminal. A plurality of output pins increases the flexibility in the data collection from the base plate.

The plurality of electrodes may include a third electrode, the third electrode comprising a third connection part, and the N input pins include a third input pin connected to the third connection part.

The multiplexer may be configured to connect the second input pin to the second output pin in the first multiplexer configuration.

The multiplexer may be configured to connect the third input pin to the second output pin in the second multiplexer configuration.

The multiplexer may be configured to connect the first input pin to the first output pin and the third input pin to the second output pin in a third multiplexer configuration.

The multiplexer may be configured to apply at least three different multiplexer configurations, such as at least four different multiplexer configurations or at least eight different multiplexer configurations. For a given multiplexer configuration, the multiplexer connects an input pin of the multiplexer to the first output pin and optionally another input pin is connected to the second output pin (if present).

The multiplexer may have at least eight input pins allowing data collection from eight electrodes on the base plate with six-terminal first connector (two terminals used for data and four terminals used for control of multiplexer configuration). The disclosed base plate allows for a large number of electrodes on the base plate while at the same time keeping the number of terminals in the first connector (monitor interface) to a minimum.

The plurality of electrodes may include a ground electrode, the ground electrode comprising a ground connection part. The N input pins may include a ground input pin connected to the ground connection part. In one or more exemplary base plates, the monitor interface comprises a plurality of terminals including a ground terminal, wherein the ground connection part is connected to the ground terminal. In one or more exemplary base plates, the multiplexer is configured to connect the ground input pin to the second output pin in one or a plurality of multiplexer configurations. In an exemplary first multiplexer configuration, the first input pin is connected to the first output pin and the ground pin is connected to the second output pin. In an exemplary second multiplexer configuration, the second input pin is connected to the first output pin and the ground pin is connected to the second output pin. In an exemplary third multiplexer configuration, the third input pin is connected to the first output pin and the ground pin is connected to the second output pin. In an exemplary fourth primary multiplexer configuration, the fourth input pin is connected to the first output pin and the ground pin is connected to the second output pin. In an exemplary fourth secondary multiplexer configuration, the fourth input pin is connected to the first output pin and the fifth input pin is connected to the second output pin. In an exemplary fourth tertiary multiplexer configuration, the fifth input pin is connected to the first output pin and the ground pin is connected to the second output pin.

The multiplexer may comprise one or more, such as three or four control pins for controlling the multiplexer configuration applied by the multiplexer. The multiplexer may comprise a first control pin. The multiplexer is optionally configured to select a multiplexer configuration based on a first control signal on the first control pin. The monitor interface may comprise a first control terminal connected to the first control pin. The multiplexer may comprise a second control pin. The multiplexer may be configured to select a multiplexer scheme based on a second control signal on the second control pin. The monitor interface may comprise a second control terminal connected to the second control pin. Thereby, a monitor device connected to the base plate can control the data collection from the base plate by applying a control signal to one or more control terminal(s) of the monitor interface. A base plate with a multiplexer allows for selecting and assigning different electrode pairs to the output pins of the multiplexer, e.g. as controlled by a monitor device. Further, a base plate with multiplexer facilitates a base plate with many electrodes, e.g. eight or more, while keeping the number of monitor terminals to a reasonable number, e.g. eight or less, such as four, five, six or seven.

The base plate may comprise a counter circuit, such as a 3-bit or 4-bit counter connected to the control pins of the multiplexer for sequentially shifting through the multiplexer configurations, e.g. based on a clock signal via the monitor interface. Such implementation may be advantageous in only requiring four terminals in the monitor interface (two data terminals and two control terminals).

In one or more exemplary base plates, wherein the number N of input pins is a least four, and wherein the base plate comprises at least four electrodes, each electrode comprises a connection part connected to an input pin of the N input pins.

Further, a method of manufacturing a base plate of an ostomy appliance is disclosed, the method comprising: providing a first adhesive layer with a proximal side configured for attachment of the base plate to the skin surface of a user; arranging a plurality of electrodes on a distal side of the first adhesive layer, the plurality of electrodes including a first electrode and a second electrode, the first electrode comprising a first connection part and the second electrode comprising a second connection part; arranging a multiplexer on the distal side of the first adhesive layer, such that input pins of the multiplexer are connected to respective connecting parts of the plurality of electrodes; arranging a monitor interface on the distal side of the first adhesive layer, the monitor interface comprising a coupling part and a plurality of terminals including a first terminal for forming mechanical and electrical connection with a monitor device, such that at least a first output pin of the multiplexer is connected to the first terminal.

Also, a method of monitoring a base plate of an ostomy appliance is disclosed, the base plate comprising a first adhesive layer, a plurality of electrodes on a distal side of the first adhesive layer, and a multiplexer, the plurality of electrodes including a first electrode and a second electrode, the method comprising: selecting a first multiplexer configuration of the multiplexer with a monitor device connected to a monitor interface of the base plate, wherein the first electrode of the base plate in the first multiplexer configuration is connected to a first terminal of the monitor interface; obtaining a first sensor signal (first ostomy data) from the first terminal of the monitor device; selecting a second multiplexer configuration of the multiplexer with the monitor device connected to the monitor interface of the base plate, wherein the second electrode of the base plate in the second multiplexer configuration is connected to the first terminal of the monitor interface; and obtaining a second sensor signal (second ostomy data) from the first terminal of the monitor device.

The base plate comprises a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening with a center point.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm, such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes, e.g. some or all the electrodes, may be arranged on distal side of the first adhesive layer. The electrodes may be arranged in an electrode assembly, e.g. an electrode layer. An electrode comprises a connection part for connecting the electrodes to other components, such as the multiplexer, and/or interface terminals. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode and/or a seventh electrode. The base plate, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly may have a stomal opening with a center point. In one or more exemplary base plates, the plurality of electrodes is arranged in an electrode assembly of the base plate, and the multiplexer is optionally embedded in the electrode assembly.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate. The multiplexer may be embedded in the coupling part of the monitor interface. For example, the first output pin of the multiplexer may be connected to first terminal element (first terminal) of the monitor interface. The second output pin of the multiplexer may be connected to the second terminal element (second terminal) of the monitor device.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A first terminal of the monitor interface may be configured as a first data terminal for collecting ostomy data from the base plate via the first terminal. A second terminal of the monitor interface may be configured as a second data terminal for collecting ostomy data from the base plate via the first terminal and the second terminal. One or more terminals of the monitor interface may be configured as one or more control terminals, respectively connected to the control pins of the multiplexer. For example, first control pin of multiplexer may be connected to third terminal of the monitor interface, the third terminal forming a first control terminal. For example, a second control pin of multiplexer may be connected to fourth terminal of the monitor interface, the fourth terminal forming a second control terminal. For example, a third control pin of the multiplexer may be connected to fifth terminal of the monitor interface, the fifth terminal forming a third control terminal. A ground connection part of the ground electrode may be connected to the ground terminal, i.e. the ground terminal may be configured as the second data terminal.

A ground control pin of the multiplexer may be connected to the ground terminal of the monitor interface, the ground terminal forming a ground control terminal of the monitor interface.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate coupled to the first interface. The ostomy data may comprise one or more, such as all, of first ostomy data from a first electrode pair of the base plate, second ostomy data from a second electrode pair of the base plate, and third ostomy data from a third electrode pair of the base plate. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by or at least may comprise:

$$(P\_1\_1<TH\_1\_1),$$

$$(P\_2\_1>TH\_1\_2), \text{ and}$$

$$(P\_3\_1>TH\_1\_3),$$

wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate. The first threshold values (TH_1_1, TH_1_2 and TH_1_3) may be the same or different, e.g. depending on the electrode configuration of the base plate. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate.

The second primary parameter may be indicative of the resistance between the second electrode pair (second electrode and second electrode part of the ground electrode) of the base plate.

The third primary parameter may be indicative of resistance between the third electrode pair (third electrode and third electrode part of the ground electrode) of the base plate.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by or at least may comprise:

$$(P\_1\_1<TH\_2\_1),$$

$$(P\_2\_1<TH\_2\_2), \text{ and}$$

$$(P\_3\_1>TH\_2\_3)$$

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate. The second threshold values (TH_2_1, TH_2_2 and TH_2_3) may be the same or different, e.g. depending on the electrode configuration of the base plate. The second primary criterion (P_1_1<TH_2_1) and/or the second tertiary criterion (P_3_1>TH_2_3) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by or at least may comprise:

$$(P\_1\_1>TH\_D\_1),$$

$$(P\_2\_1>TH\_D\_2), \text{ and}$$

$$(P\_3\_1>TH\_D\_3)$$

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate has experienced a third degree of radial erosion, e.g. the first adhesive layer is eroded to the third radial distance of the third electrode pair.

The third criteria set may be given by or at least may comprise:

$$(P\_1\_1<TH\_3\_1),$$

$$(P\_2\_1<TH\_3\_2), \text{ and}$$

$$(P\_3\_1<TH\_3\_3)$$

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate. The third threshold values (TH_3_1, TH_3_2 and TH_3_3) may be the same or different, e.g. depending on the electrode configuration of the base plate. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by $$(P\_4\_1<TH\_4\_4)$$

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g.

the monitor device may form an integrated part of a base plate of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a stoma center point 19. The size and/or shape of the stomal opening 18 is typically adjusted by the user or nurse before application of the ostomy appliance to accommodate the user's stoma.

Figure 2:
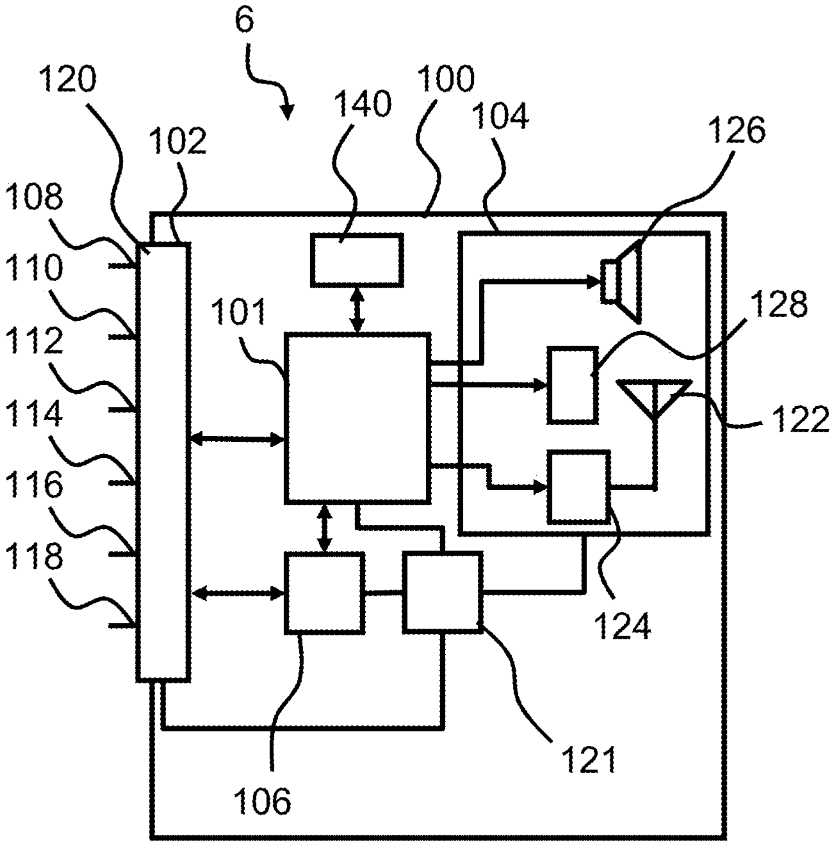
FIG. 2 illustrates an exemplary monitor device of the ostomy system.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. The sensor unit 140 comprises a temperature sensor for feeding temperature data to the processor and/or a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

The monitor device 6 controls which electrodes of the base plate 2 are connected to first terminal 110 and second terminal 112. The first terminal 110 and the second terminal 112 of monitor device are configured as data terminals and ostomy data of the base plate are collected from the first terminal 110 and the second terminal 112 connected to first terminal and second terminal, respectively, of the base plate, when the base plate is coupled to the monitor device. Ground terminal 108, third terminal 114, fourth terminal 116, and fifth terminal 118 are configured/used as control terminals. The monitor device 6 is configured to select or apply a plurality of multiplexer configurations in the multiplexer of the base plate by sending different control signals to the control terminals of the base plate, e.g. "001" for the first multiplexer configuration and/or "010" for the second multiplexer configuration.

Figure 3:
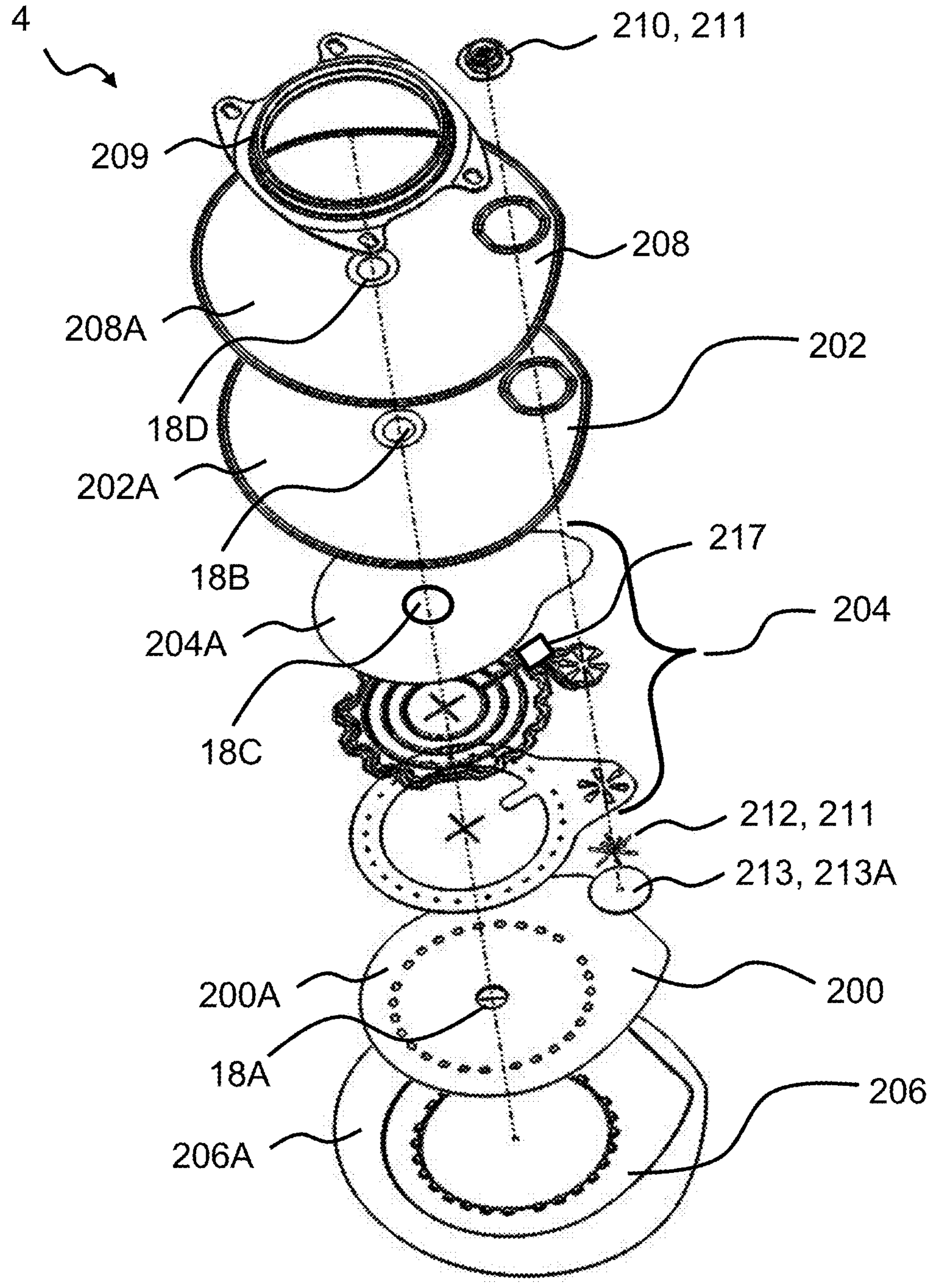
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202 with a stomal opening 18B. The electrode assembly 204 comprises a support layer with a stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
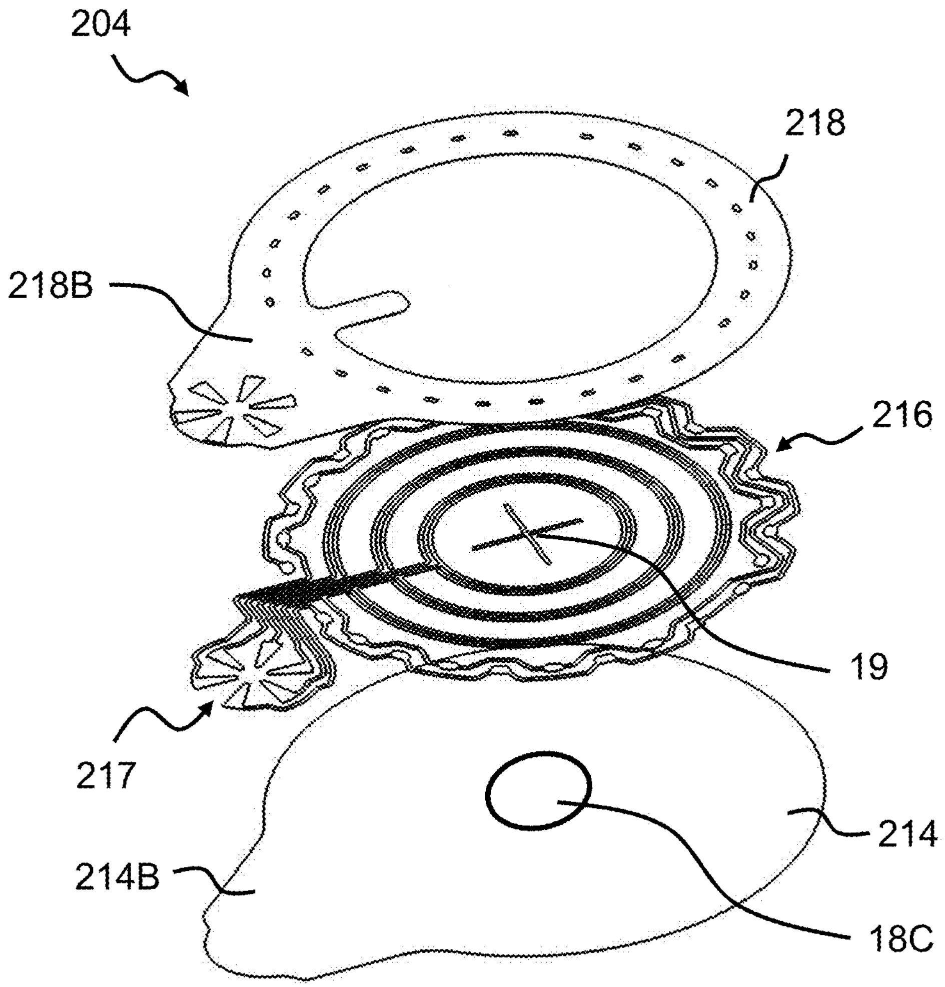
FIG. 4 is an exploded view of an exemplary electrode assembly.

FIG. 4 illustrates an exploded view of an exemplary electrode assembly 204 of a base plate. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part. The electrode assembly comprises a multiplexer 217 with input pins of the multiplexer 217 connected to connection parts of the electrodes. Output pins and control pins of the multiplexer 217 are connected to terminal connection parts 221 for connecting the output pins and control pins of multiplexer 217 to respective terminal elements of the monitor interface. Further, electrode assembly 204 comprises a masking element 218 with proximal surface 218B and configured to insulate electrode parts of electrodes 216 from the first adhesive layer of the base plate. The masking element 218 covers or overlaps with parts of the electrodes 216 when seen in the axial direction.

Figure 5:
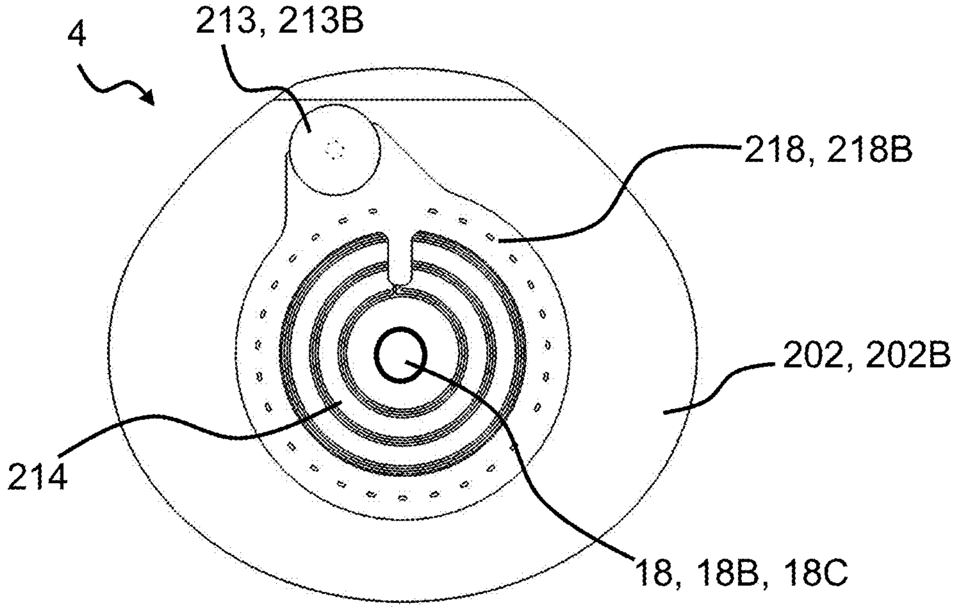
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
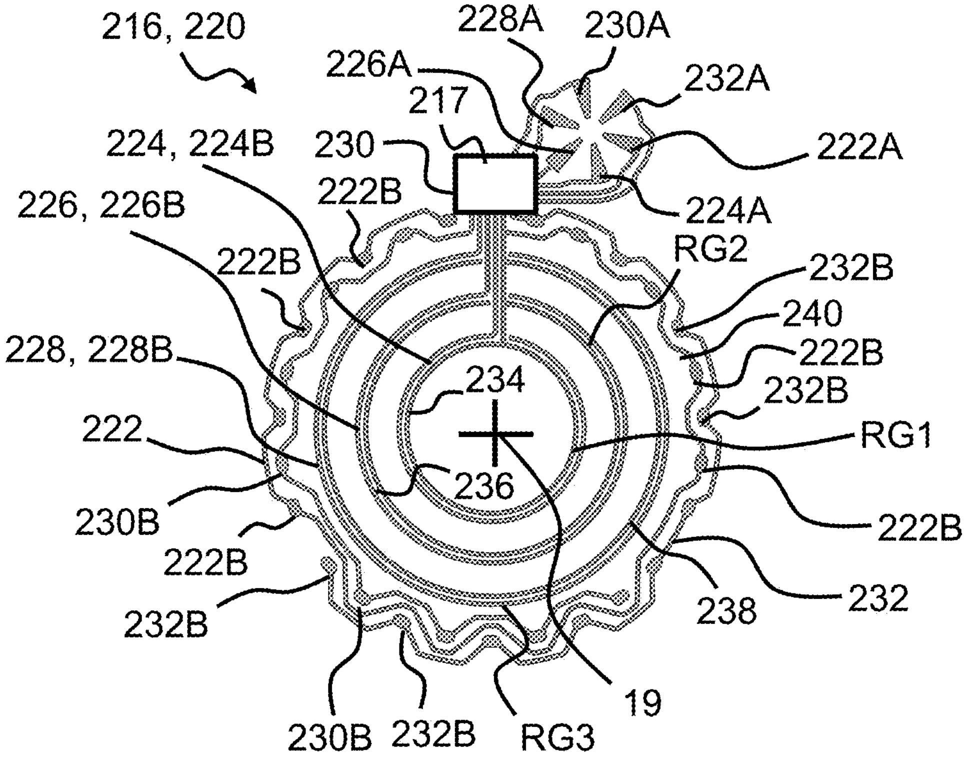
FIG. 6 is a distal view of an exemplary electrode configuration.

FIG. 6 is a distal view of an exemplary electrode configuration 220 of electrodes 216 of the electrode assembly 204 including multiplexer 217. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part connected to a ground input pin of the multiplexer 217 and the first electrode 224 comprises a first connection part connected to a first input pin of the multiplexer 217. The second electrode 226 comprises a second connection part connected to a second input pin of the multiplexer 217 and the third electrode 228 comprises a third connection part connected to a third input pin of the multiplexer 217. The fourth electrode 230 comprises a fourth connection part connected to a fourth input pin of the multiplexer 217 and the fifth electrode 232 comprise a fifth connection part connected to a fifth input pin of the multiplexer 217. The multiplexer 217 comprises a first output pin connected to first terminal connection part 224A, and a second output pin connected to the second terminal connection part 226A. The first terminal connection part 224A is connected to first terminal of the first connector, see FIG. 10, thus connecting the first output pin and the first terminal of the monitor interface. The second terminal connection part 226A is connected to second terminal of the first connector, see FIG. 10, thus connecting the second output pin and the second terminal of the monitor interface.

The multiplexer comprises a ground control pin connected to ground terminal connection part 222A. The ground terminal connection part 222A is connected to ground terminal of the first connector, see FIG. 10, thus connecting the ground control pin and the ground terminal of the monitor interface. The multiplexer 217 comprises a first control pin connected to third terminal connection part 228A. The third terminal connection part 228A is connected to third terminal of the first connector, see FIG. 10, thus connecting the first control pin and the third terminal of the monitor interface. The multiplexer 217 comprises a second control pin connected to fourth terminal connection part 230A. The fourth terminal connection part 230A is connected to fourth terminal of the first connector, see FIG. 10, thus connecting the second control pin and the fourth terminal of the monitor interface. The multiplexer 217 comprises a third control pin connected to fifth terminal connection part 232A. The fifth terminal connection part 232A is connected to fifth terminal of the first connector, see FIG. 10, thus connecting the third control pin and the fifth terminal of the monitor interface. Thus, ground terminal, third terminal, fourth terminal, and fifth terminal of first connector (monitor interface) form ground control terminal, first control terminal, second control terminal, and third control terminal, respectively.

The multiplexer 217 is configured to connect the first input pin (first electrode 224) to the first output pin (i.e. to the first terminal of monitor interface) in a first multiplexer configuration and to connect the second input pin (second electrode 226) to the first output pin (i.e. to the first terminal of monitor interface) in a second multiplexer configuration. The multiplexer selects between multiplexer configurations based on control signals on the control terminals.

The control signals can be received from monitor device connected to the first connector of the base plate, thus allowing a monitor device to select a desired multiplexer configuration.

In the first multiplexer configuration, the multiplexer 217 is configured to connect the second input pin or the ground input pin to the second output pin.

The fourth electrode 230 comprises fourth sensing parts 230B. The fifth electrode 232 comprises fifth sensing parts 232B.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

Figure 7:
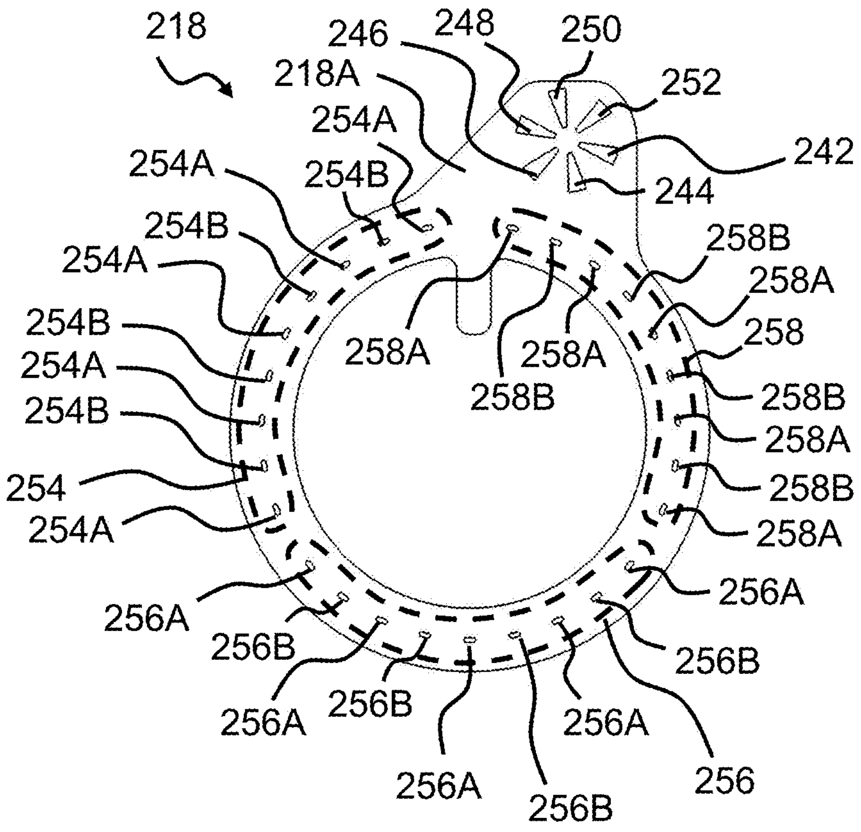
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
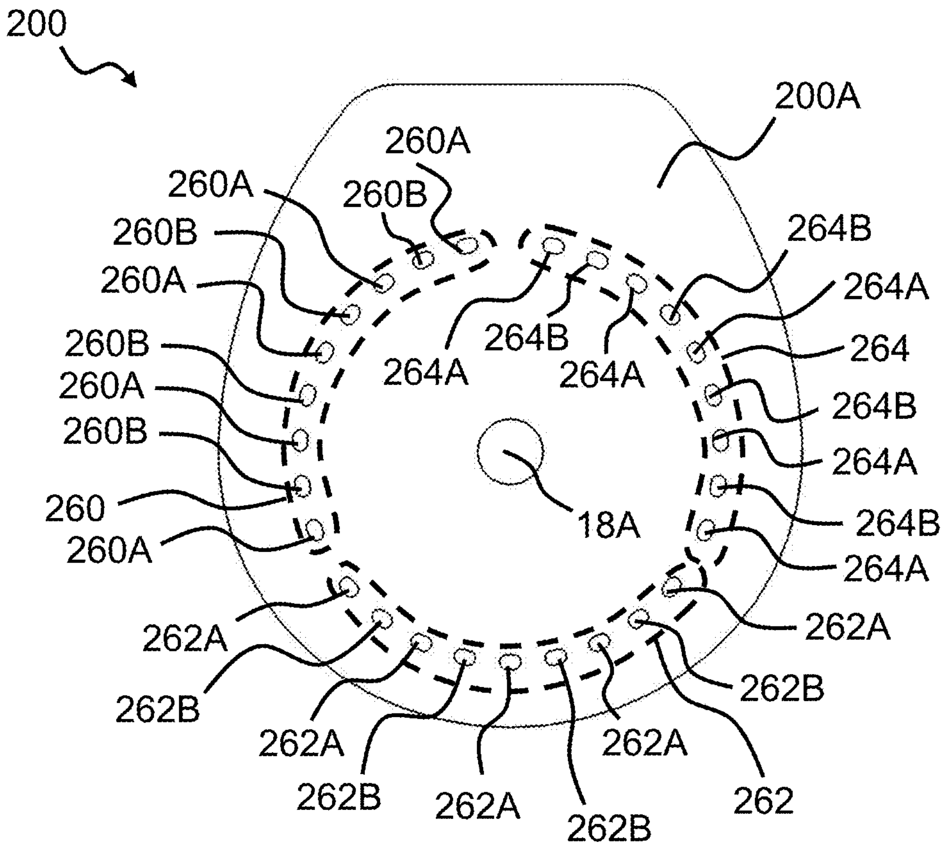
FIG. 8 is a distal view of an exemplary first adhesive layer.
Figure 9:
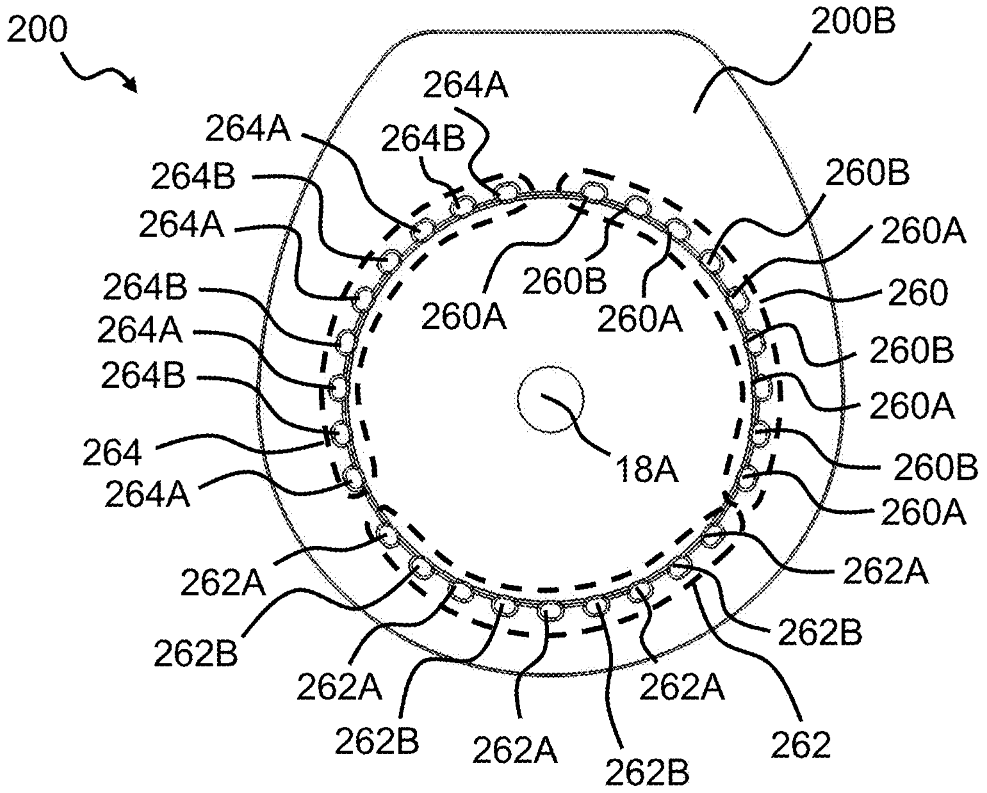
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
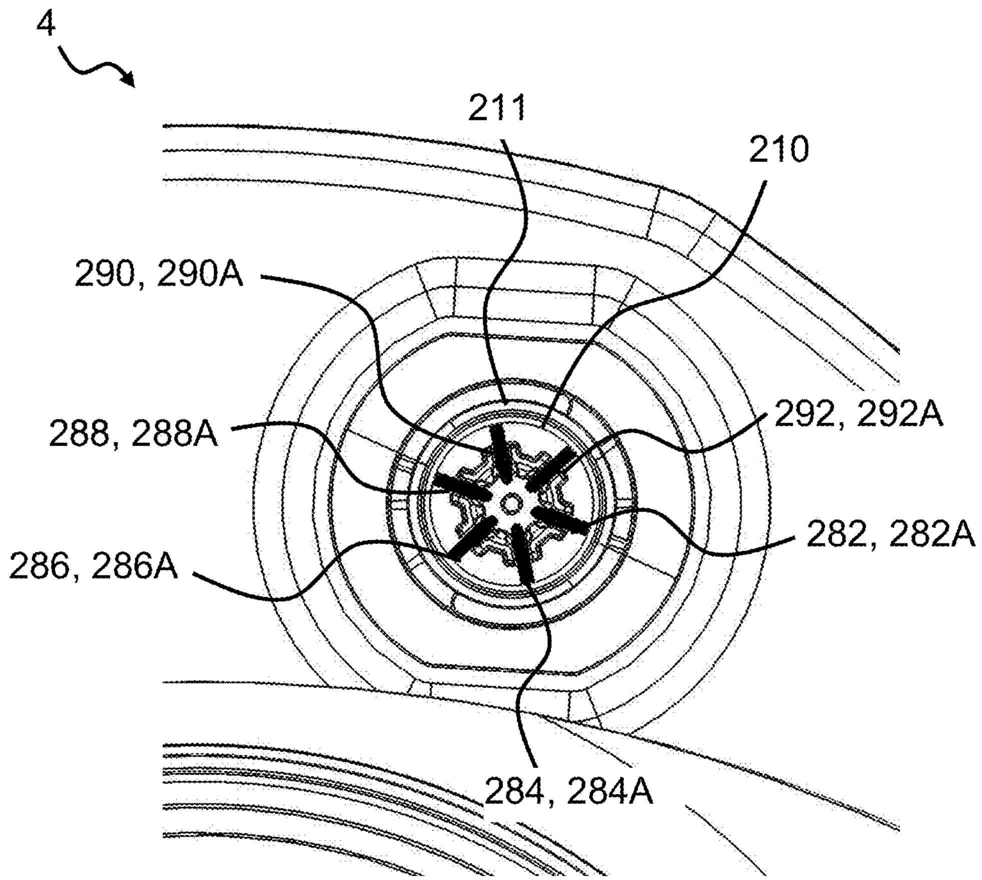
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/monitor interface comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230*a*, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
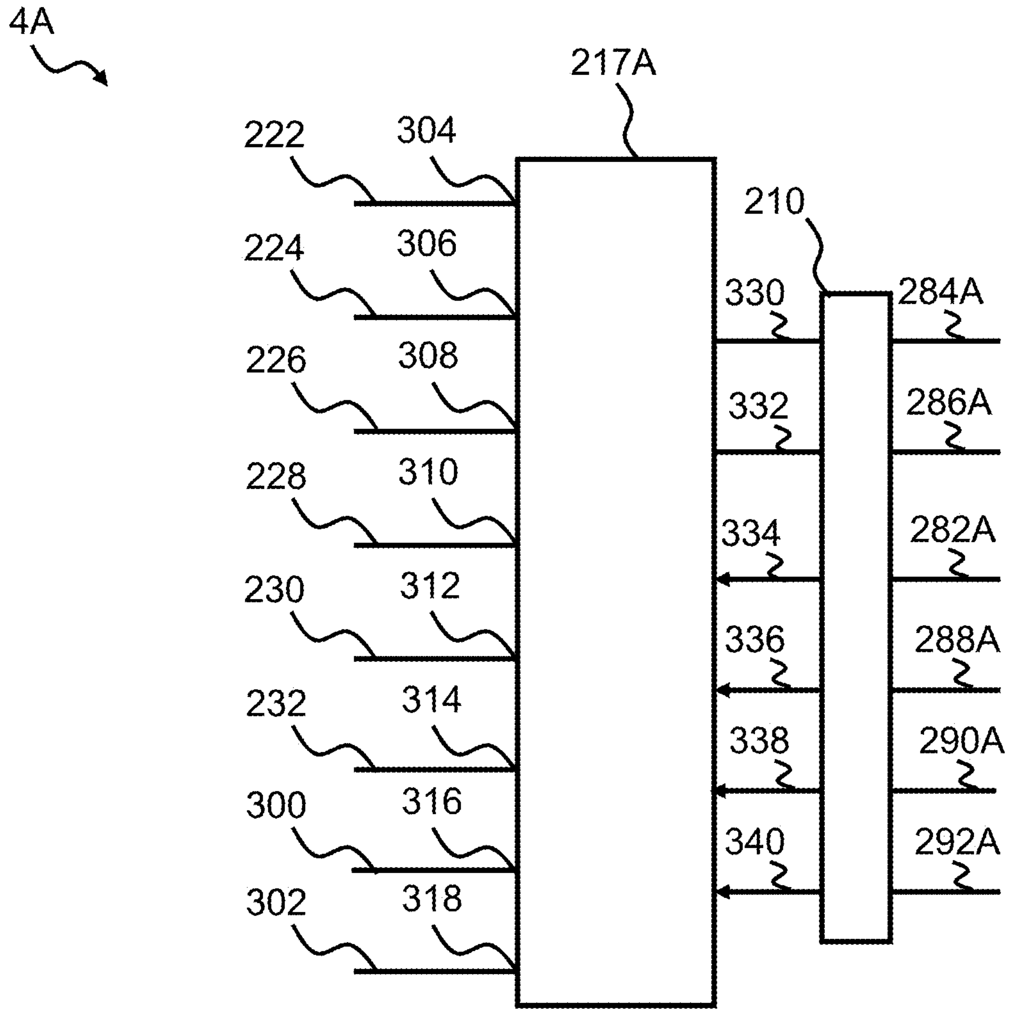
FIG. 11 shows a part of an exemplary base plate.

FIG. 11 schematically shows a part of an exemplary base plate 4A. The base plate 4A comprises eight electrodes 222, 224, 226, 228, 230, 232, 300, 302 with respective connection parts 304, 306, 308, 310, 312, 314, 316, 318 connected to respective input pins of the multiplexer 217A. The multiplexer 217A comprises a first output pin 330 connected to first terminal 284A of the first connector of monitor interface. The multiplexer 217A comprises a second output pin 332 connected to second terminal 286A of the first connector of monitor interface. The multiplexer 217A comprises a ground control pin 334 connected to ground terminal 282A of the first connector of monitor interface. The multiplexer 217A comprises a first control pin 336 connected to third terminal 288A of the first connector of monitor interface. The multiplexer 217A comprises a second control pin 338 connected to fifth terminal 290A of the first connector of monitor interface. The multiplexer 217A comprises a third control pin 340 connected to fifth terminal 292A of the first connector of monitor interface. With the base plate 4A, it is possible to collect data from eight different electrode pairs in eight different multiplexer configurations via a six-terminal connector with free choice of both electrodes.

Figure 12:
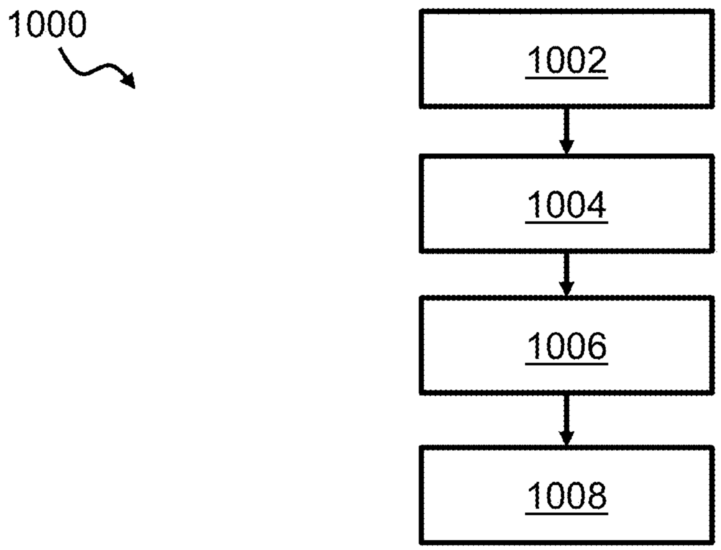
FIG. 12 is a flow chart of an exemplary method.

FIG. 12 is a flow chart of an exemplary method of manufacturing a base plate of an ostomy appliance. The method 1000 comprises providing 1002 a first adhesive layer, e.g. first adhesive layer 200, with a proximal side configured for attachment of the base plate, e.g. base plate 4, 4A, to the skin surface of a user; arranging 1004 a plurality of electrodes on a distal side of the first adhesive layer, the plurality of electrodes including a first electrode, e.g. first electrode 224, and a second electrode, e.g. second electrode 226, the first electrode comprising a first connection part and the second electrode comprising a second connection part; arranging 1006 a multiplexer, e.g. multiplexer 217, 217A, on the distal side of the first adhesive layer, such that input pins of the multiplexer are connected to respective connecting parts of the plurality of electrodes; arranging 1008 a monitor interface on the distal side of the first adhesive layer, the monitor interface comprising a coupling part, e.g. coupling part 210, and a plurality of terminals including a first terminal, e.g. first terminal 284A, for forming mechanical and electrical connection with a monitor device, e.g. monitor device 6, such that at least a first output pin of the multiplexer is connected to the first terminal.

Figure 13:
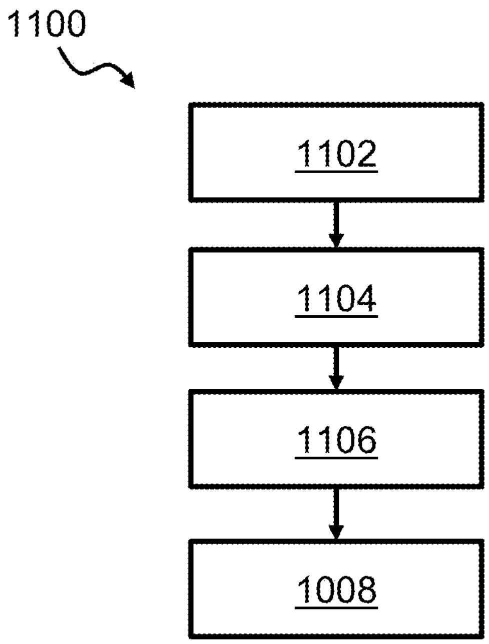
FIG. 13 is a flow chart of an exemplary method.

FIG. 13 is a flow chart of an exemplary method of monitoring a base plate, e.g. base plate 4, 4A, of an ostomy appliance, the base plate comprising a first adhesive layer, e.g. first adhesive layer 200, a plurality of electrodes on a distal side of the first adhesive layer, and a multiplexer, e.g. multiplexer 217, 217A, the plurality of electrodes including a first electrode, e.g. first electrode 224, and a second electrode, e.g. second electrode 226. The method 1100 comprises selecting 1102 a first multiplexer configuration of the multiplexer with a monitor device connected to a monitor interface of the base plate, wherein the first electrode of the base plate in the first multiplexer configuration is connected to a first terminal of the monitor interface; obtaining 1104 a first sensor signal (first ostomy data) from the first terminal of the monitor device; selecting 1106 a second multiplexer configuration of the multiplexer with the monitor device connected to the monitor interface of the base plate, wherein the second electrode of the base plate in the second multiplexer configuration is connected to the first terminal of the monitor interface; and obtaining 1108 a second sensor signal (second ostomy data) from the first terminal of the monitor device.

Also disclosed are base plates and methods according to any of the following items.

Item 1. A base plate for an ostomy appliance, the base plate comprising:

- a first adhesive layer with a proximal side configured for attachment of the base plate to the skin surface of a user;
- a plurality of electrodes including a first electrode and a second electrode, the first electrode comprising a first connection part and the second electrode comprising a second connection part;
- a monitor interface for forming mechanical and electrical connection with a monitor device, the monitor interface comprising a coupling part and a plurality of terminals including a first terminal; and
- a multiplexer with a number of N input pins and a number of M output pins;
- wherein the N input pins includes a first input pin and a second input pin, and the M output pins include a first output pin,
- wherein the first input pin is connected to the first connection part and the second input pin is connected to the second connection part, and the first output pin is connected to the first terminal of the monitor interface, and wherein the multiplexer is configured to connect the first input pin to the first output pin in a first multiplexer configuration and to connect the second input pin to the first output pin in a second multiplexer configuration.

Item 2. A base plate according to item 1, wherein the monitor interface comprises a second terminal, and wherein the M output pins include a second output pin connected to the second terminal.

Item 3. A base plate according to any of items 1-2, wherein the plurality of electrodes includes a third electrode, the third electrode comprising a third connection part, and the N input pins include a third input pin connected to the third connection part.

Item 4. A base plate according to any of items 2-3, wherein the multiplexer is configured to connect the second input pin to the second output pin in the first multiplexer configuration.

Item 5. A base plate according to any of items 2-4 as dependent on item 3, wherein the multiplexer is configured to connect the third input pin to the second output pin in the second multiplexer configuration.

Item 6. A base plate according to any of items 2-5 as dependent on item 3, wherein the multiplexer is configured to connect the first input pin to the first output pin and the third input pin to the second output pin in a third multiplexer configuration.

Item 7. A base plate according to any of the items 1-6, wherein the multiplexer comprises a first control pin, and wherein the multiplexer is configured to select a multiplexer configuration based on a first control signal on the first control pin.

Item 8. A base plate according to item 7, wherein the monitor interface comprises a first control terminal connected to the first control pin.

Item 9. A base plate according to any of the items 1-8, wherein the multiplexer comprises a second control pin, and wherein the multiplexer is configured to select a multiplexer scheme based on a second control signal on the second control pin, and wherein the monitor interface comprises a second control terminal connected to the second control pin.

Item 10. A base plate according to any of the items 1-9, wherein the plurality of electrodes is arranged in an electrode assembly of the base plate, and wherein the multiplexer is embedded in the electrode assembly.

Item 11. A base plate according to any of the items 1-10, wherein the multiplexer is embedded in the coupling part of the monitor interface.

Item 12. A base plate according to any of the items 1-11, wherein the number N of input pins is a least four, and wherein the base plate comprises at least four electrodes, each electrode comprising a connection part connected to an input pin.

Item 13. A method of manufacturing a base plate of an ostomy appliance, the method comprising:

providing a first adhesive layer with a proximal side configured for attachment of the base plate to the skin surface of a user;

arranging a plurality of electrodes on a distal side of the first adhesive layer, the plurality of electrodes including a first electrode and a second electrode, the first electrode comprising a first connection part and the second electrode comprising a second connection part;

arranging a multiplexer on the distal side of the first adhesive layer, such that input pins of the multiplexer are connected to respective connecting parts of the plurality of electrodes;

arranging a monitor interface on the distal side of the first adhesive layer, the monitor interface comprising a coupling part and a plurality of terminals including a first terminal for forming mechanical and electrical connection with a monitor device, such that at least a first output pin of the multiplexer is connected to the first terminal.

Item 14. A method of monitoring a base plate of an ostomy appliance, the base plate comprising a first adhesive layer, a plurality of electrodes on a distal side of the first adhesive layer, and a multiplexer, the plurality of electrodes including a first electrode and a second electrode, the method comprising:

selecting a first multiplexer configuration of the multiplexer with a monitor device connected to a monitor interface of the base plate, wherein the first electrode of the base plate in the first multiplexer configuration is connected to a first terminal of the monitor interface;

obtaining a first sensor signal from the first terminal of the monitor device;

selecting a second multiplexer configuration of the multiplexer with the monitor device connected to the monitor interface of the base plate, wherein the second electrode of the base plate in the second multiplexer configuration is connected to the first terminal of the monitor interface; and obtaining a second sensor signal from the first terminal of the monitor device.

The use of the terms “first”, “second”, “third” and “fourth”, “primary”, “secondary”, “tertiary” etc. does not imply any particular order, but are included to identify individual elements. Moreover, the use of the terms “first”, “second”, “third” and “fourth”, “primary”, “secondary”, “tertiary” etc. does not denote any order or importance, but rather the terms “first”, “second”, “third” and “fourth”, “primary”, “secondary”, “tertiary” etc. are used to distinguish one element from another. Note that the words “first”, “second”, “third” and “fourth”, “primary”, “secondary”, “tertiary” etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

1 ostomy system
2 ostomy appliance
4, 4A base plate
6 monitor device
8 accessory device
10 server device
12 network
14 coupling member

16 coupling ring
18, 18A, 18B, 18C, 18D stomal opening
19 center point
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217, 217A multiplexer
218 masking element
218A distal surface of masking element
218B proximal surface of masking element
220 electrode configuration
221 terminal connection parts
222 ground electrode
222A ground terminal connection part
222B ground sensing part
224 first electrode
224A first terminal connection part
226 second electrode
226A second terminal connection part
228 third electrode
228A third terminal connection part
230 fourth electrode
230A fourth terminal connection part
230B fourth sensing part
232 fifth electrode
232A fifth terminal connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
300 sixth electrode
302 seventh electrode
304 ground connection part
306 first connection part
308 second connection part
310 third connection part
312 fourth connection part
314 fifth connection part
316 sixth connection part
318 seventh connection part
330 first output pin
332 second output pin
334 ground control pin
336 first control pin
338 second control pin
340 third control pin
1000 method of manufacturing a base plate of an ostomy appliance
1002 providing a first adhesive layer
1004 arranging a plurality of electrodes on a distal side of the first adhesive layer

1006 arranging a multiplexer on the distal side of the first adhesive layer

1008 arranging a monitor interface on the distal side of the first adhesive layer

1100 method of monitoring a base plate of an ostomy appliance

1102 selecting a first multiplexer configuration of the multiplexer

1104 obtaining a first sensor signal from the first terminal of the monitor device

1106 selecting a second multiplexer configuration of the multiplexer

1108 obtaining a second sensor signal from the first terminal of the monitor device

The invention claimed is:

1. A base plate for an ostomy appliance, the base plate comprising:

an adhesive layer with a proximal side configured for attachment to a skin surface of a user;

a plurality of electrodes disposed on a distal side of the adhesive layer;

a monitor interface comprising a plurality of terminals for connection with a monitor device, the plurality of terminals including a first terminal, a second terminal, and a control terminal; and a multiplexer configured to switchably couple the first terminal and the second terminal of the monitor interface with an electrode of the plurality of electrodes according to a control signal received via the control terminal, wherein:

according to a first multiplexer configuration indicated by the control signal, the multiplexer couples a first electrode of the plurality electrodes to the first terminal and a second electrode of the plurality of electrodes to the second terminal; and according to a second multiplexer configuration indicated by the control signal, the multiplexer couples a third electrode of the plurality electrodes to the first terminal and a fourth electrode of the plurality of electrodes to the second terminal.

2. The base plate of claim 1, wherein:

the first electrode is a ground electrode;

the ground electrode and the second electrode cooperate to form a first sensor; and the multiplexer couples the ground electrode to the first terminal and a third electrode of the plurality of electrodes to the second terminal in a second multiplexer configuration, wherein the ground electrode and the third electrode cooperate to form a second sensor.

3. The base plate of claim 2, wherein, in a third multiplexer configuration, the multiplexer couples a fourth electrode of the plurality of electrodes to the second terminal in a second multiplexer configuration and the ground electrode and the fourth electrode cooperate to form a third sensor.

4. The base plate of claim 1, wherein:

the control terminal is a first control terminal;

the monitor interface further comprises a second control terminal; and the control signal is received via the first control terminal and the second control terminal.

5. The base plate of claim 1, wherein the multiplexer is embedded in a coupling part of the monitor interface.

6. The base plate of claim 1, wherein the plurality of electrodes is arranged in an electrode assembly of the base plate, and the multiplexer is embedded in the electrode assembly.

7. The base plate of claim 1, wherein the second electrode is the fourth electrode.

8. A base plate for an ostomy appliance, the base plate comprising:

an adhesive layer with a proximal side configured for attachment to a skin surface of a user;

a plurality of electrodes disposed on a distal side of the adhesive layer, the plurality of electrodes comprising: a common electrode, a first electrode, and a second electrode;

a monitor interface configured to couple the base plate to a monitor device, the monitor interface comprising:

a common terminal coupled to the common electrode;

a first terminal coupled to a multiplexer; and a control terminal; and the multiplexer, configured to switchably couple the first terminal with at least the first electrode or the second electrode according to a control signal received via the control terminal, wherein:

the multiplexer couples the first terminal and the first electrode in a first multiplexer configuration indicated by the control signal, thereby causing the first electrode and the common electrode to form a first sensor readable via the common terminal and the first terminal; and the multiplexer couples the first terminal and the second electrode in a second multiplexer configuration indicated by the control signal, thereby causing the second electrode and the common electrode to form a second sensor readable via the common terminal and the first terminal.

9. The base plate of claim 8, wherein the multiplexer couples the first terminal and a third electrode of the plurality of electrodes in a third multiplexer configuration indicated by the control signal, thereby causing the third electrode and the common electrode to form a third sensor readable via the common terminal and the first terminal.

10. The base plate of claim 8, wherein:

the control terminal is a first control terminal;

the monitor interface further comprises a second control terminal; and the control signal is received via the first control terminal and the second control terminal.

11. The base plate of claim 8, wherein the common terminal is coupled to the common electrode via the multiplexer in the first multiplexer configuration.

12. The base plate of claim 11, wherein the common terminal is coupled to a third electrode in the second multiplexer configuration.

13. The base plate of claim 8, wherein:

the plurality of electrodes further comprises a third electrode, a fourth electrode, and a fifth electrode; and the multiplexer is configured to switchably couple the first terminal further with the third electrode, the fourth electrode, and the fifth electrode.

14. The base plate of claim 8, wherein the plurality of electrodes is arranged in an electrode assembly comprising a support layer, and the multiplexer is embedded in the electrode assembly.

15. An ostomy monitoring system comprising:

a base plate comprising:

an adhesive layer;

a plurality of electrodes;

a monitor interface comprising a plurality of terminals for connection with the monitor device, the plurality of terminals including a first terminal, a second terminal, and a control terminal; and a multiplexer configured to switchably couple the first terminal and the second terminal of the monitor interface with an electrode of the plurality of electrodes according to a control signal received via the control terminal, wherein:

according to a first multiplexer configuration indicated by the control signal, the multiplexer couples a first electrode of the plurality of electrodes to the first terminal and a second electrode of the plurality of electrodes to the second terminal; and according to a second multiplexer configuration indicated by the control signal, the multiplexer couples a third electrode of the plurality of electrodes to the first terminal and a fourth electrode of the plurality of electrodes to the second terminal; and a monitor device configured to releasably couple to the monitor interface, the monitor device configured to:

provide the first control signal to the control terminal to select the first multiplexer configuration; and provide the second control signal to the control terminal to select the second multiplexer configuration of the multiplexer.

16. The ostomy monitoring system of claim 15, wherein, according to a third multiplexer configuration indicated by the control signal, the multiplexer couples a fifth electrode of the plurality of electrodes to the first terminal and a sixth electrode of the plurality of electrodes to the second terminal.

17. The ostomy monitoring system of claim 15, wherein the monitor device is further configured to obtain sensor signals via the first terminal and the second terminal and to process the sensor signals to determine an operating state indicative of a degree of radial erosion of the adhesive layer.

18. The ostomy monitoring system of claim 15, wherein the plurality of electrodes is arranged in an electrode assembly of the base plate, and the multiplexer is embedded in the electrode assembly.

19. The ostomy monitoring system of claim 15, wherein the second electrode is the fourth electrode.

20. The ostomy monitoring system of claim 15, wherein the control terminal is a first control terminal, the monitor interface further comprises a second control terminal, and the monitor device provides the first control signal and the second control signal via the first control terminal and the second control terminal.

* * * * *